United States Patent [19]
Horiba

[11] 4,253,770
[45] Mar. 3, 1981

[54] OPTOACOUSTIC ANALYZER

[75] Inventor: Atsushi Horiba, Kyoto, Japan

[73] Assignee: Horiba, Ltd., Kyoto, Japan

[21] Appl. No.: 927,095

[22] Filed: Jul. 24, 1978

[30] Foreign Application Priority Data

Aug. 26, 1977 [JP] Japan ................... 52/103091

[51] Int. Cl.³ ............................................ G01N 21/59
[52] U.S. Cl. .................................... 356/433; 250/343; 356/437
[58] Field of Search ................... 356/323, 433, 437; 250/343, 344, 345

[56] References Cited

U.S. PATENT DOCUMENTS

| | | | |
|---|---|---|---|
| 3,911,276 | 10/1975 | Bell | 250/343 |
| 4,019,056 | 4/1977 | Block et al. | 250/344 |
| 4,058,725 | 11/1977 | Aine | 250/343 |
| 4,059,356 | 11/1977 | Kebabian | 250/343 |

OTHER PUBLICATIONS

Deaton et al., *Applied Physics Letters*, vol. 26, No. 14, Dec. 1973, pp. 300-303.

Latz et al., *Analytical Chemistry*, vol. 45, No. 14, Dec. 1973, pp. 2405-2409.

*Primary Examiner*—F. L. Evans
*Attorney, Agent, or Firm*—McCoy & Granger Pearne, Gordon, Sessions

[57] ABSTRACT

An optoacoustic analyzer which allows the light from a laser resonator to enter a differential cell assembly can not provide accurate measurement of a specific component of ultralow concentration because the laser light, as it passes through the sample chamber and reference chamber, is absorbed to cause significant attenuation and the adverse effect of a low concentration of an inhibitory component in the fluid sample can not be effectively eliminated. Further, this type of anaylzer receives the laser light at the detector after it has passed through mirrors, and therefore, only few percents of the light within the resonator reaches the detector, thus providing only low sensitivity. To solve these problems, the differential cell type, light transmitting, optoacoustic analyzer of this invention has the sample chamber and reference chamber disposed on the beam path between the resonating mirrors in the gas laser resonator.

4 Claims, 7 Drawing Figures

OPTOACOUSTIC ANALYZER

This invention relates to an optoacoustic analyzer using laser light, and more particularly, to an analyzer that is capable of providing stable and accurate measurement of substances of ultralow concentrations such as pollutants in the atmosphere, specific components of a solid, etc.

Heretofore, heated nichrome wire has been typically used as the optical source for infrared absorption analysis. But recently, laser light has been drawing attention as the effective optical source for measuring substances of extremely low concentrations because it has high monochromaticity, produces high output and has good directivity. FIGS. 1 and 2 each shows a conventional type of analytic apparatus that uses laser light as the light source. According to an apparatus of the type shown in FIG. 1, laser light emitted from a gas laser resonator 1 is caused to irradiate (or pass through) a sample chamber 2 and reference chamber 3 of a differential cell type, light transmitting, optoacoustic detector. This type of detector however requires laser light of high energy because the light emitted from the resonator 1 has its energy attenuated in the process of transmission, and secondly, the accuracy of measurement falls just short of perfection because absorption of light by windows 4 and 5 causes an error.

According to an apparatus of the type described in FIG. 2, a sample cell 6 is disposed within a gas laser resonator 7, and a detector 8 outside the resonator. In this case, the error due to a window 9 may be negligible, but since this is not an apparatus of differential cell type, the adverse effect of any inhibitory component of low concentration in a sample gas is difficult to eliminate (the differential cell type requires a complicated double beam system). Further, compared with the amount of light existing in the resonator, the light that reaches the detector 8 through a mirror 10 is only few percents, thus resulting in so much reduced sensitivity.

All of these defects encountered in the conventional technique has been eliminated from this invention, which is characterized by disposing the sample chamber and reference chamber of a differential cell type, light transmitting, optoacoustic detector within a gas laser resonator having a laser discharge tube and a pair of resonating mirrors.

According to the analyzer of this invention which accommodates both a sample chamber and reference chamber within a resonator, no attenuation of the laser light that is passing through these chambers takes place, thus providing high sensitivity and obviating the need of using a laser light of high energy. In addition, the provision of the chambers within the resonator results in higher accuracy of measurement because no error will occur due to the absorption of energy by windows. As a further advantage, the detector of this invention which is of differential cell type allows effective elimination of the adverse effect of an inhibitory component of low concentration in a sample. What is more, if a specific component of a sample gas is to be analyzed by diluting the sample gas with a base gas and sealing such sample gas into the sample chamber while sealing only the base gas into the reference chamber, the amount of energy absorbed by the base gas is equal between the two chambers, thus permitting recovering as an output that amount of the sample which exactly corresponds to the energy absorbed. Furthermore, the error of measurement due to inhibitory components can be eliminated by sealing into the reference chamber the gas obtained by removing the target component of the sample with the aid of an absorption tube, combustion tube or so forth.

The preferred embodiments of this invention are now described by reference to the accompanying drawings.

Figure 3:
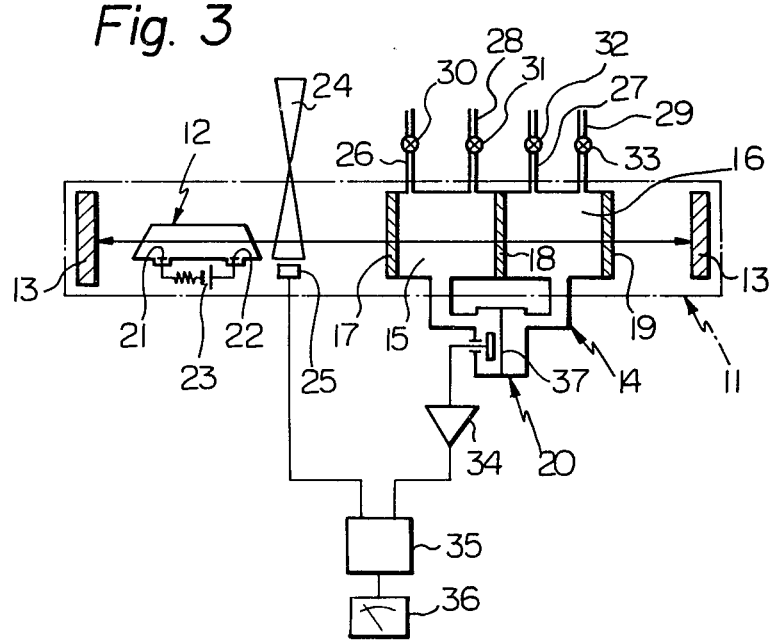
FIG. 3 is an illustration showing one embodiment of this invention.

FIG. 3 shows the first embodiment of this invention, or an optoacoustic analyzer for measuring a low concentration of methane $CH_4$ contained in a sample gas (for instance, the ambient atmosphere). In the Figure, 11 is a gas laser resonator accommodating a laser discharge tube 12 filled with He-Ne gas and a pair of resonating mirrors 13, 13; 14 is a differential cell type, light transmitting, optoacoustic detector equipped with a sample chamber 15, a reference chamber 16, windows 17, 18 and 19, and a capacitor microphone 20. As the Figure shows, the sample chamber 15 and reference chamber 16 are disposed within the laser resonator 11. The reference numerals 21 and 22 are electrodes; 23 is a high voltage source; 24 is a chopper provided in the laser resonator 11; 25 is a sync signal detector; 26 and 27 are gas introducing passageways; 28 and 29 are gas discharging passageways; 30, 31, 32 and 33 are valves; 34 is a preamplifier; 35 is a lock-in amplifier; and 36 is an indicator.

According to the arrangement illustrated above, the light emitted from the laser discharge tube 12 is resonated with the mirrors 13, 13 to produce a laser light having a wavelength of 3.39 μm. The laser light passes through the sample chamber 15 and reference chamber 16 disposed within the resonator 11. The light is also interrupted by the chopper 24 at a specified frequency and a.c. converted for the purpose of stabilized processing of signals.

The sample chamber 15 of the detector 14 is charged with the atmosphere containing a low concentration of methane $CH_4$ through the passageway 26, and the reference chamber 16 charged through the passageway 27 with $N_2$ gas which does not absorb the laser light above or the atmosphere from which $CH_4$ has been removed using an oxidizing catalyst. Each chamber is then made tight by closing the valves 30 to 33. The laser light with which the sample chamber 15 has been irradiated is absorbed by $CH_4$ gas that has an absorption band at 3.39 μm, the wavelength of the laser light; the temperature of the sample gas then increases in proportion to the concentration of $CH_4$ it contains, which in turn increases the pressure of the gas. On the other hand, no pressure build-up occurs in the reference chamber 16 which is free from $CH_4$. As a result, a difference in pressure develops between the two chambers 15 and 16 and moves the membrane 37 of the capacitor microphone. The movement is amplified by the preamplifier 34, synchronized and rectified with a signal from the sync signal detector 36 so as to actuate the indicator 36.

Figure 1:
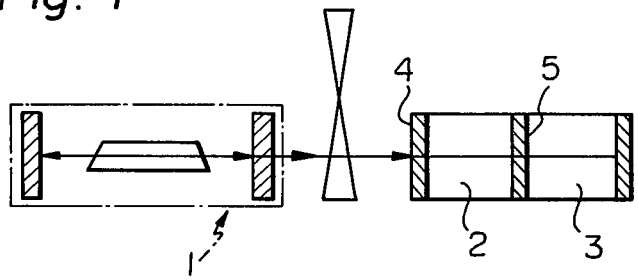
FIGS. 1 and 2 are each an illustration of a conventional apparatus.
Figure 2:
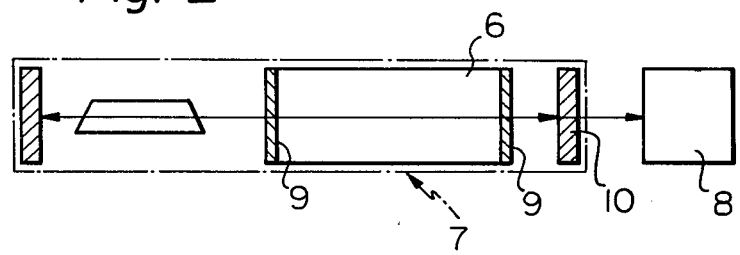
Figure 4:
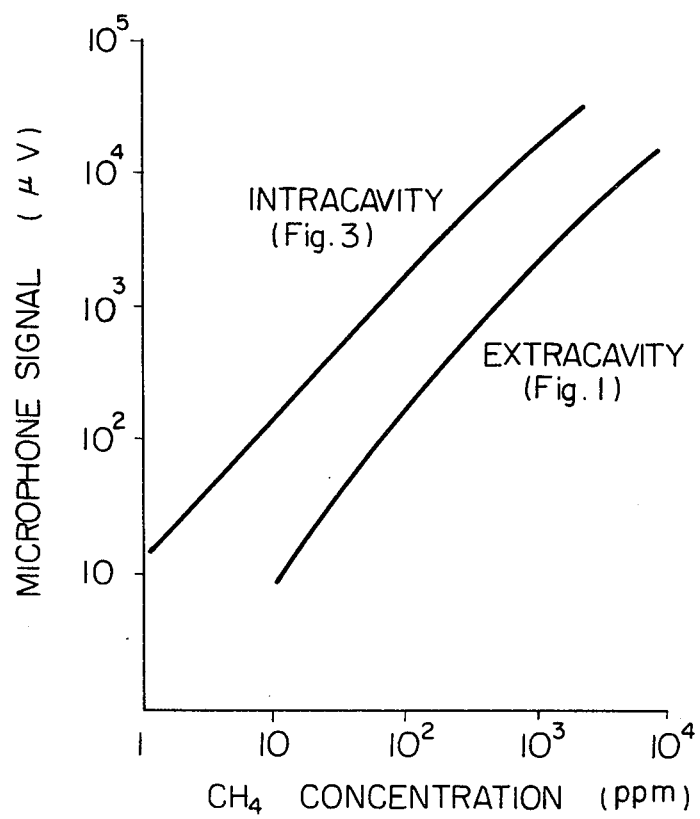
FIG. 4 is a graph showing the results of experiments using a conventional apparatus and the apparatus according to this invention.

As FIG. 4 shows, the embodiment described above provides sensitivity more than 10 times higher than in the case of operating the conventional apparatus of the type described in FIG. 1 from the same excitation energy.

Figure 5:
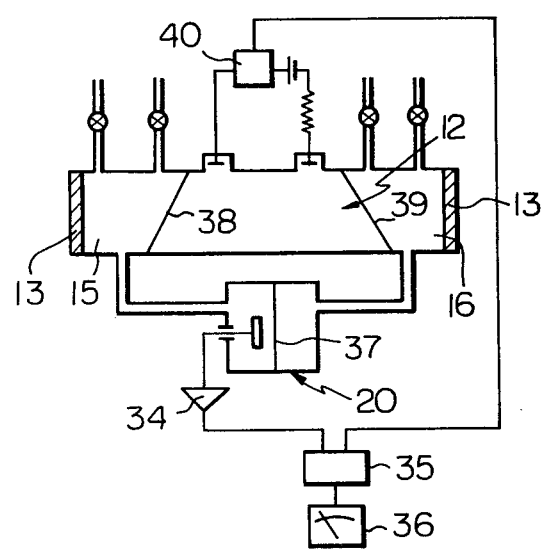
FIG. 5 is an illustration showing another embodiment of this invention.

FIG. 5 shows the second embodiment of this invention, wherein the windows 17, 18 and 19 that define the sample chamber 15 and reference chamber 16 are absent, and instead, the end walls 38, 39 of the laser discharge tube 12 and the resonating mirrors 13, 13 are used to define the two chambers; a discharge interrupter 40 replaces the chopper 24 for interrupting the emission of light from the laser discharge tube 12 and issuing a signal to the lock-in amplifier 35 for synchronization and rectification purposes. The members the same as those used in the first embodiment are referred to by the same numerals and their explanation is therefore omitted.

Figure 6:
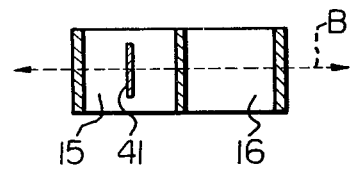
FIGS. 6 and 7 are each an illustration showing the essential part of another embodiment of this invention.
Figure 7:
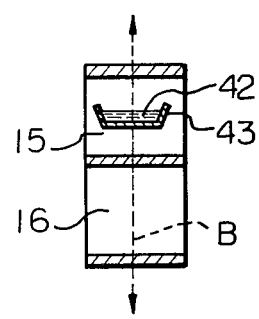

Both first and second embodiments illustrated above relate to the analysis of gas, but it should of course be understood that this invention is applicable to the analysis of liquid or solid, emulsion and suspension. For analysis of a solid, as illustrated in FIG. 6, a sliced sample is placed in the sample chamber 15 which a laser light B passes through as indicated by the dotted line, and both the sample chamber 15 and reference chamber 16 are filled with a gaseous thermal expansion medium such as $N_2$ gas. If a liquid is to be analyzed, as shown in FIG. 7, a sample 42 is placed in a vessel 43 made of a material through which the laser of a specified wavelength can pass and placed in the sample chamber 15, and both the sample chamber 15 and reference chamber 16 are filled with a gaseous thermal expansion medium such as $N_2$ gas. For both cases, this invention is capable of eliminating the adverse effect of impurities present in the gaseous thermal expansion medium.

What we claim is:

1. An optoacoustic analyzer comprising a gas laser resonator defined by two resonator mirrors, a gas laser discharge tube including spaced windows located within said resonator, an optoacoustic detector including a sample chamber and a reference chamber which are disposed in the path of laser light between the resonator mirrors, the laser discharge tube being arranged between the sample chamber and the reference chamber, each of the chambers being defined on one side by one of the resonating mirrors and on the other side by one of the windows of the discharge tube, the sample and reference chambers cooperating to form a differential cell and to provide a detector output signal which represents the pressure difference between the sample and the reference chamber due to the different absorption of the laser light in the chambers, a discharge interrupter associated with the gas laser discharge tube to provide an interrupter output signal which is passed to a lock-in amplifier to rectify the detector output signal in synchronization with the interrupter output signal.

2. An optoacoustic analyzer according to claim 1 wherein each of said sample chamber and reference chamber of said detector is provided with a fluid introducing passageway and a fluid discharging passageway.

3. An optoacoustic analyzer according to claim 2 wherein a gas is sealed in said sample chamber and/or reference chamber.

4. An optoacoustic analyzer according to claim 2 wherein a solid or liquid sample is placed in said sample chamber.

* * * * *